(12) United States Patent
Lovick et al.

(10) Patent No.: US 10,806,826 B2
(45) Date of Patent: Oct. 20, 2020

(54) BONE GRAFT SUBSTITUTE CONTAINING A TEMPORARY CONTRAST AGENT AND A METHOD OF GENERATING SUCH AND A METHOD OF USE THEREOF

(71) Applicant: BACTERIN INTERNATIONAL, INC., Belgrade, MT (US)

(72) Inventors: Helena Lovick, Belgrade, MT (US); Gregory Juda, Bozeman, MT (US); Todd Meyer, Bozeman, MT (US)

(73) Assignee: BACTERIN INTERNATIONAL, INC., Belgrade, MT (US)

( * ) Notice: Subject to any disclaimer, the term of this patent is extended or adjusted under 35 U.S.C. 154(b) by 553 days.

(21) Appl. No.: 14/758,815

(22) PCT Filed: Jan. 9, 2014

(86) PCT No.: PCT/US2014/010916
§ 371 (c)(1),
(2) Date: Jul. 1, 2015

(87) PCT Pub. No.: WO2014/110284
PCT Pub. Date: Jul. 17, 2014

(65) Prior Publication Data
US 2015/0374883 A1 Dec. 31, 2015

Related U.S. Application Data (60) Provisional application No. 61/750,600, filed on Jan. 9, 2013.

(51) Int. Cl.
| | | |
|---|---|---|
| *A61L 27/50* | (2006.01) | |
| *A61K 51/12* | (2006.01) | |
| *A61L 27/46* | (2006.01) | |
| *A61K 49/04* | (2006.01) | |
| *A61L 27/14* | (2006.01) | |
| *A61L 27/22* | (2006.01) | |
| *A61L 27/24* | (2006.01) | |
| *A61L 27/36* | (2006.01) | |
| *A61L 27/54* | (2006.01) | |
| *A61L 27/58* | (2006.01) | |

(52) U.S. Cl.
CPC .......... *A61L 27/50* (2013.01); *A61K 49/0433* (2013.01); *A61K 51/12* (2013.01); *A61L 27/14* (2013.01); *A61L 27/225* (2013.01); *A61L 27/24* (2013.01); *A61L 27/3608* (2013.01); *A61L 27/46* (2013.01); *A61L 27/54* (2013.01); *A61L 27/58* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,405,402 A | 4/1995 | Dye et al. | |
| 5,505,932 A * | 4/1996 | Grinstaff | A61K 49/126 |
| | | | 424/9.3 |
| 5,508,021 A | 4/1996 | Grinstaff et al. | |
| 5,532,420 A * | 7/1996 | Drivon | C07C 17/204 |
| | | | 570/170 |
| 5,676,146 A | 10/1997 | Scarbourough | |
| 5,795,911 A | 8/1998 | Cheng et al. | |
| 6,161,034 A | 12/2000 | Burbank et al. | |
| 7,417,077 B2 | 8/2008 | Lidgren et al. | |
| 7,510,579 B2 | 3/2009 | Preissman | |
| 7,598,219 B2 | 10/2009 | Zanella et al. | |
| 7,637,948 B2 | 12/2009 | Corbitt, Jr. | |
| 7,883,511 B2 | 2/2011 | Fernyhough | |
| 7,972,630 B2 | 7/2011 | Lidgren | |
| 8,157,862 B2 | 4/2012 | Corbitt, Jr. | |
| 2004/0157952 A1 | 8/2004 | Soffiati et al. | |
| 2005/0036945 A1 | 2/2005 | Thomas et al. | |
| 2006/0004440 A1 | 1/2006 | Stinson | |
| 2006/0008504 A1 | 1/2006 | Kerr et al. | |
| 2007/0003593 A1 | 1/2007 | Wironen et al. | |
| 2007/0191964 A1 | 8/2007 | Preissman | |
| 2008/0008654 A1 | 1/2008 | Clarke et al. | |
| 2008/0214998 A1 | 9/2008 | Kurek et al. | |
| 2008/0305145 A1 | 12/2008 | Shelby et al. | |
| 2011/0070312 A1 | 3/2011 | Wei et al. | |
| 2012/0116515 A1 | 5/2012 | Semler et al. | |
| 2012/0121660 A1 | 5/2012 | Akella et al. | |
| 2012/0234718 A1 | 9/2012 | Schense et al. | |
| 2012/0251609 A1 | 10/2012 | Huang et al. | |

FOREIGN PATENT DOCUMENTS

EP          2311471          4/2011

OTHER PUBLICATIONS

Hallouard et al. Radiopaque iodinated nano-emulsions for preclinical x-ray imaging. 2011 RSC Advances 1: 792-801. (Year: 2011).*
Mattrey "Perfluorooctylbromide: a new contrast agent for CT, sonography, and MR imaging," American Journal of Roentgenology, Feb. 1989, vol. 152, No. 2, pp. 247-252.
Flaim et al. "Influence of Perflubron Emulsion Particle Size on Blood Half-Life and Febrile Response in Rats," Artificial Cells, Blood Substitutes, and Immobilization Biotechnology, 1994, vol. 22, No. 4, pp. 1169-1174 (Abstract Only).
Leese et al. "Randomized Safety Studies of Intravenous Perflubron Emulsion. I. Effects on Coagulation Function in Healthy Volunteers," Anesthesia & Analgesia, Oct. 2000, vol. 91, No. 4, pp. 804-811.

(Continued)

*Primary Examiner* — Jennifer Lamberski (57) ABSTRACT

A bone graft substitute for use in orthopedic bone grafting procedures comprising a radiolucent bone graft substitute combined with a temporary radiopaque agent. Methods of making and using the composition are also disclosed. Bone graft substitutes have become an effective means of regenerating bone in orthopedic procedures where bone loss results from surgically created defects or traumatic injury to the bone. Bone graft substitutes include mineral-based materials such as hydroxyapatite, calcium phosphates, and calcium phosphosilicates as well as allograft-derived materials and xenograft-derived materials such as collagen-based matrices and demineralized bone matrices.

49 Claims, 2 Drawing Sheets

(56) References Cited

OTHER PUBLICATIONS

International Search Report and Written Opinion for International (PCT) Patent Application No. PCT/US2014/010916, dated Mar. 21, 2014 22 pages.
International Preliminary Report on Patentability for International (PCT) Patent Application No. PCT/US2014/010916, dated Jul. 23, 2015 20 pages.

* cited by examiner

BONE GRAFT SUBSTITUTE CONTAINING A TEMPORARY CONTRAST AGENT AND A METHOD OF GENERATING SUCH AND A METHOD OF USE THEREOF

CROSS REFERENCE TO RELATED APPLICATIONS

This application is a national stage application under 35 U.S.C. 371 and claims the benefit of PCT Application No. PCT/US2014/010916 having an international filing date of 09 Jan. 2014, which designated the United States, which PCT application claimed the benefit and priority under 35 U.S.C. § 119(e) to U.S. Provisional Application Ser. No. 61/750,600 filed Jan. 9, 2013, each of which are incorporated herein in their entirety by reference.

FIELD OF THE INVENTION

This invention relates to a bone graft substitute material containing a temporary radiopaque material and methods for making and using the same.

BACKGROUND

Bone graft substitutes have become an effective means of regenerating bone in orthopedic procedures where bone loss results from surgically created defects or traumatic injury to the bone. Bone graft substitutes include mineral-based materials such as hydroxyapatite, calcium phosphates, and calcium phosphosilicates as well as allograft-derived materials and xenograft-derived materials such as collagen-based matrices and demineralized bone matrices.

Demineralized bone matrix (DBM) is a common bone graft substitute that is manufactured via removal of the mineral content of cortical or cancellous bone resulting in a substantially mineral-free collagen scaffold containing collagen-bound growth factors. Due to the presence of biologically active growth factors, DBM has the ability to induce de novo bone when implanted into a non-bony site in an athymic mouse or rat. While it is unknown how the osteoinductivity potential in this assay correlates with human clinical performance, this assay serves as the most accurate and commonly used measure of osteoinductive potential of bone graft substitutes to date. DBM may be human-derived (allogeneic) or animal-derived (xenogeneic) and is available in a variety of compositions including gels, putties, strips, and combinations with other bone graft substitutes or carriers.

Solid bony fusion is highly radiopaque relative to a bone void or a radiolucent bone graft. Some bone graft substitutes, such as synthetic calcium phosphate bone grafts, are visible via X-ray spectroscopy at the time of implantation and throughout the healing process. Radiopacity during placement aids the surgeon's assessment of graft placement. Unfortunately, this radiopacity often hinders assessment of bone healing due to remaining radiopaque graft material in the months or years following implantation. For example, hydroxyapatite-based radiopaque graft materials take a substantial amount of time to remodel and may remain in a relatively unchanged state for several years after implantation. Meanwhile, DBM is radiolucent providing a distinct advantage during follow-up assessment of bone formation since any radiographic density at the previous void or bone defect is indicative of new bone formation. DBM is generally remodeled within a few months after implantation. Consequently, standard orthopedic follow-up times of three to six months for DBM implants allow for accurate assessment of post-operative bone growth. Aside from DBM, other bone graft substitutes that appear radiolucent during implantation include many biodegradable polymers, collagen scaffolds, fibrin scaffolds, and several thermoplastics.

The radiolucency of DBM and other radiolucent bone graft substitutes, however, does not allow for assessment of the bone graft placement at the time of surgery using standard radiographic methods. This is especially disadvantageous when placing graft material during a minimally invasive surgical procedure in a percutaneous fashion. In these cases, it is highly desirable for the operating surgeon to be able to visualize placement of the bone graft substitute, as the operative site is not directly visible. In order to solve this inherent drawback, it is the object of this invention to combine a bone graft substitute with a temporary radiopaque agent or marker to allow visualization of graft placement during minimally invasive surgical procedures conducted under fluoroscopy. The temporary marker combined with a bone graft substitute is designed to dissipate over time resulting in a radiolucent implant thus allowing accurate assessment of bone fusion after a standard post-operative time period.

SUMMARY OF THE INVENTION

The present invention discloses an implant composed of a bone graft substitute and a temporary radiopaque agent or marker that allows for visualization of the implant under fluoroscopy or other medical imaging during surgical implantation. The radiopaque agents disclosed dissipate from the surgical site over time to allow ease of post-operative assessment of bone healing. The radiopaque agent may be used with the bone graft substitute alone, in combination with the bone graft substitute and other radiopaque agents, in combination with the bone graft substitute, other bioactive agents, and/or various carriers or additives. Additionally, methods of generating the implant and a method for surgical use of the implant are disclosed.

An aspect of the present invention is a method for repairing a bone defect in a patient, comprising implanting a composition comprising a bone graft substitute and a temporary radiopaque agent in a bone defect of a patient, visualizing placement of the composition by imaging the composition in the bone defect, and assessing repair of the bone defect by imaging the bone defect after the temporary radiopaque agent has at least partially dissipated.

Another aspect of the present invention is a method of preparing a bone implant containing a temporary radiopaque agent, comprising contacting a bone graft substitute with the temporary radiopaque agent, wherein the temporary radiopaque agent is in a form selected from the group consisting of a neat solution, an undiluted solution, an emulsion, a suspension, a slurry, and a gel, and wherein the bone graft substitute is radiolucent.

Still another aspect of the present invention is a composition comprising a radiolucent bone graft substitute and a temporary radiopaque agent, wherein the temporary radiopaque agent dissipates in less than about one month after the composition is implanted in a patient.

DETAILED DESCRIPTION

The present invention relates to a bone graft substitute containing a temporary radiopaque agent, a method for making the same and a method for using the same.

"Allogeneic" or "allograft", as used herein, refers to human-derived tissue intended for transplantation.

"Biocompatible" as used herein refers to the property of being biologically compatible with a living being by not producing harm.

The term "biodegradable," as used herein, refers to matter capable of being broken down by biological and/or environmental processes.

As used herein, the term "fluoroscopy" refers to medical imaging that uses X-rays to obtain images of internal structures of a patient.

The terms "fluoroscopic dye," "radiopaque marker," "radiopaque agent" and "contrast agent" are used interchangeably herein to refer to substances that are visible during various medical imaging techniques including, but not limited to, X-ray fluoroscopy, X-ray computed tomography (CT), magnetic resonance imaging (MRI), and ultrasound.

The term "neat" as used herein, refers to an undiluted substance.

The term "xenogeneic" or "xenograft", as used herein, refers to animal-derived tissue intended for transplantation between animals of different species.

As used herein, the term "bone defect" is defined as a void, fracture or space existing in the skeletal system of a patient.

The term "bone graft substitute" as used herein, is defined as a material used to fill a bone defect in a patient. In many instances, the bone graft substitute allows for bone formation in the bone defect.

The term "dissipate(s)" as used herein, refers to a material leaving a physical location, such as by migrating to another location, by absorption, and/or by degrading. As used herein, the temporary radiopaque agent dissipates from a site following imaging of a bone defect repair. The term "temporary radiopaque agent" as used herein, is defined as a radiopaque agent which may be used to view an object containing or coated with the temporary radiopaque agent for a period of time. After the time has elapsed, the temporary radiopaque agent dissipates. The period of time may be between about 30 minutes to about one month.

The term "radiopaque" as used herein, is defined as being visible to various forms of radiation and/or medical imaging techniques.

The term "radiolucent" as used herein, is defined as being almost entirely transparent to, or almost invisible to, radiation and/or medical imaging techniques.

An object of this invention is a composition and method of making an implant of composition containing a bone graft substitute and a temporary radiopaque agent, such as a fluoroscopic dye, that allows for visualization of graft material placement under fluoroscopy during minimally invasive orthopedic surgery or other implantation procedures. A further embodiment of the invention is a method for surgical use of a bone implant or composition comprising a temporary radiopaque agent and a bone graft substitute that provides initial medical imaging visualization followed by subsequent monitoring of bone fusion, unimpeded, during and following the bone healing process. In various embodiments of the present invention, the bone implant or composition for implanting in a bone defect can comprise between about 1% by weight to about 99.9% by weight, about 5% by weight to about 95% by weight, about 30% by weight to about 90% by weight, about 40% by weight to about 85% by weight, or about 50% by weight to about 80% by weight of a bone graft substitute.

In the various embodiments, the bone implant or composition for implanting in a bone defect can comprise between about 0.1% by weight to about 99% by weight, about 1% by weight to about 95% by weight, about 5% by weight to about 85% by weight, about 10% by weight to about 80% by weight, or about 20% by weight to about 70% by weight of a temporary radiopaque agent.

Suitable bone graft substitutes in several aspects and embodiments of the invention include, but are not limited to, any radiolucent biodegradable polymers, biodegradable polymer mixtures, collagen scaffolds, fibrin scaffolds, thermoplastics and/or demineralized bone matrix (DBM). Radiolucent biodegradable polymers or copolymers may include, but are not limited to, alginate, hyaluronate, polycaprolactones, polyethylene glycols, polyhydroxyalkanoates, polyesteramides, polylactides, polyglycolides, poly(lactide-co-glycolide)s, polyorthoesters, polyoxazolines, and polyurethanes. The radiolucent biodegradable polymers can be used alone or in combination with one another. Radiolucent thermoplastics that may be used for this invention include, but are not limited to, polyethyl ether ketone (PEEK), polyethylenes, and polyurethanes. In some embodiments, the bone graft substitute may be a DBM and may be allogeneic, xenogeneic, cancellous, and/or cortical. The bone graft substitute described in this invention may be in an intact shape such as a block, cone, strip, cylinder, wafer, bone putty, bone paste, shredded fibers, crushed bone particles, a plurality of ground bone particles, or combinations thereof. In embodiments where the bone graft substitute is ground or crushed, the average size of the particles may be between about 0.2 mm to about 15 mm. Some examples of suitable DBM and methods of making the same are described in U.S. Publication No. 2008/0305145, filed on May 30, 2008, which is incorporated by reference in its entirety. The DBM may be partially or fully demineralized such that the mineral content is between about 1% to about 90% of an original mineral content of the material.

Suitable temporary radiopaque agents include, but are not limited to, fluoroscopic dyes based on or containing barium, bismuth, iodine, gadolinium, perfluorocarbons (PFC), perfluorinated hydrocarbons and combinations thereof. The radiopaque agents have a sufficient half-life to visualize the implant containing the temporary radiopaque agent placement after surgery, yet dissipate within a few minutes to months allowing for a subsequent radiographic assessment of bone formation because the new bone and/or surrounding bone is sufficiently visible or unobstructed to allow assessment. Table 1 lists several suitable radiopaque agents and the approximate associated clearance rates based on administration routes. As illustrated in Table 1, the clearance rates vary based on a combination of the radiopaque agent, the administration route and the dosage.

TABLE 1

| Radiopaque Agent | Administration Route | Dosage | Clearance/Half-life |
|---|---|---|---|
| Perfluorooctyl bromide (PFOB) | Intravascular | 1.2 g/kg | $t_{1/2}$ = 9.4 hours |
|  |  | 1.8 g/kg | $t_{1/2}$ = 6.1 hours |
| Perfluorodecalin | Intravenous |  | $t_{1/2}$ = 6 days |
| Perfluorotripropylamine | Intravenous |  | $t_{1/2}$ = 63 days |
| PFOB | Oral | 2-12 mL/kg | >95% excreted within 24 hours |
| Iohexol | Intravenous | Varies by imaging needs | $t_{1/2}$ = 30-60 minutes |
| Iohexol | Intravascular | 500-1500 mgI/kg | ~90% excreted within 24 hours |
| Gadolinium-Based Contrast ECF (extracellular fluid) Agents (e.g., Gadopenetate dimeglumine, Gadodiamide, Gadobutrol, and Gadoteridol) | Intravenous | 0.1 mmol Gd/kg | $t_{1/2}$ = 1.5 hours (normal renal function) |

The approximate clearance rates illustrated in Table 1 for radiopaque agents vary (i.e., $t_{1/2}$=6 days for perfluorodecalin versus 63 days for perfluorotripropylamine, *AJR Am J Roentgenol.* 1989, 152, 247-252). The clearance rate of radiopaque agents may be further modified by other methods. For example, the particle size of perfluorochemical emulsions inversely affects the blood half-life of the materials such that smaller emulsion particles result in longer intravascular retention (*Artif Cells Blood Substit Immobil Biotechnol.* 1994, 22, 1169-1174).

Examples of radiopaque perfluorocarbons which may be used for this invention specifically include, but are not limited to, perfluorooctyl bromide or perfluorohexyl bromide. PFCs radiopaque to $^{19}F$ magnetic resonance imaging (MRI) but not traditional fluoroscopy may be used include, but are not limited to, perfluorooctane, perfluoropentane, perfluorohexane, perfluorodecalin, perfluorotributylamine (and salts thereof), perfluorotriisopropylamine (and salts thereof), or perfluoro-crown ethers (containing 12, 15, or 18 crown ethers) or combinations thereof. Iodinated radiopaque dyes may be used and specifically include, but are not limited to, iohexol, iopamidol, ioxilan, iopromide, metrizamide, ioxaglic acid (and salts thereof), iotrolan, ioversol, iopentol, iodixanol, iomeprol, iodbitridol, lopydol, propyliodine, iofendylate, lipiodol or combinations thereof. Gadolinium-based radiopaque dyes may also be used and specifically include, but are not limited to, gadopentetic acid (or salts thereof), gadobutrol, gadofosveset, gadolinium, gadoteridol, gadoversetamide, gadoxetic acid (or salts thereof), gadoteric acid (or salts thereof), or gadobenic acid (or salts thereof) or combinations thereof. Other temporary radiopaque agents, which may be combined with DBM, include barium salts, bismuth salts and combinations thereof.

In some embodiments, the temporary radiopaque agent dissipates in between about 30 minutes and about six months, between about 1 day and about three months, and between about 1 day to about 14 days. In some embodiments, the temporary radiopaque agent dissipates in about 6 months, in about 5 months, in about 4 months, in about 3 months, in about 2 months, in about 1 month, in about 3 weeks, in about 2 weeks, in about 1 week, in about 5 days or in about 1 day.

Furthermore, the radiopaque agent may dissipate to less than about 99%, less than about 95%, less than about 90%, less than about 85%, less than about 80%, less than about 70%, less than about 60%, less than about 50%, less than about 40%, less than about 30%, less than about 20%, or less than about 10% of its original amount.

Bone implants or compositions for implanting in a bone defect may include a bioactive substance. Suitable bioactive substances including, but are not limited to, antibiotics, antimicrobials, antiseptics, antifungals, hormones, growth factors, cells, biocompatible minerals, and combinations thereof. Specific examples of biocompatible minerals include, but are not limited to, bioactive glasses (bioglass), calcium phosphate, calcium sulfate, hydroxyapatite, and combinations thereof. Specific examples of bioactive substances include, but are not limited to, bisbiguanides (including chlorhexidine and alexidine), silver nanoparticles, silver nitrate, silver oxide, silver salts, silver sulfadiazine, silver zeolites, gentamicin, vancomycin, tobramycin, triclosan, antifolates, aminoglycosides, carbapenems, cephalosporins, fluoroquinolines, glycopeptides, macrolides, monobactams, oxazolidones, penicillins, rifamycins, sulfonamides and tetracyclines and combinations thereof. Bioactive substances may be used individually or as a mixture of multiple bioactive substances. The bioactive substance may be in the form of a salt. Furthermore, bioactive substances, for example bisbiguanides, may be used in their monomer form, or polymer form.

An aspect of the present invention includes a method for repairing a bone defect in a subject. The method includes implanting a composition comprising a bone graft substitute and a temporary radiopaque agent in a bone defect of a patient, visualizing placement of the composition by imaging the composition in the bone defect, and assessing repair of the bone defect by imaging the bone defect after the temporary radiopaque agent has at least partially dissipated.

In an embodiment of the invention, the temporary radiopaque agent dissipates over the course of minutes to months so that visualization of new bone formation is unobstructed by the temporary radiopaque agent. In some embodiments, the temporary radiopaque agent dissipates within about six months, within about one month, within about fourteen days, within about seven days, within about three days, within about one day, within about four hours, and within about 30 minutes.

In some embodiments, the temporary radiopaque agent may be bound to the bone implant or the composition for implanting in a bone defect, to a carrier, and/or to an additive. The bond may be a covalent bond or an ionic bond.

In some embodiments, an additive or carrier may be bound to the bone implant or composition for implanting in a bone defect. The bond may be a covalent bond or an ionic bond. Additives may be combined to provide mixtures of radiopaque components. Possible combinations include salts of perfluorinated amine compounds (e.g., perfluorotributylamine or perfluorotriisopropylamine) with radiopaque acids (e.g., gadopentetic acid, gadoxetic acid, gadoteric acid, gadobenic acid, or ioxaglic acid. Alternatively PFCs radiolucent to traditional fluoroscopy (e.g., perfluorooctane, perfluoropentane, perfluorohexane, perfluorodecalin, perfluorotributylamine (and salts thereof), perfluorotriisopropylamine (and salts thereof), or perfluoro-crown ethers (containing 12, 15, or 18 crown ethers)) may be combined at various concentrations with other fluoroscopic, radiopaque dyes including, but not limited to, the radiopaque compounds.

Several techniques may be used to visualize, assess or image the placement of the bone implant, or the composition for implanting in a bone defect, and healing progress of the bone defect. Suitable techniques include X-ray, MRI, CT, and ultrasound, though any suitable radiation imaging technique may be used. The visualization or imaging may occur during the placement of the bone graft substitute, or within about 2 hours of the placement of the bone graft substitute. The subsequent assessment of the repair may occur within about 10 years of the placement of the bone graft substitute, within about 5 years of the placement of the bone graft substitute, within about 1 year of the placement of the bone graft substitute, within about 6 months of the placement of the bone graft substitute and within about one month of the placement of the bone graft substitute. Following placement of the bone implant or the composition for implanting in a bone defect, the radiopaque agent dissipates to the radiopacity equivalent of between about 0.01 mm of aluminum to about 0.5 mm of aluminum within about one month of the placement of the bone graft substitute. In some embodiments, the radiopaque agent dissipates to less than the radiopacity equivalent of about 0.5 mm of aluminum, less than about 0.3 mm of aluminum, less than about 0.1 mm of aluminum, less than about 0.05 mm of aluminum, less than about 0.01 mm of aluminum. The same technique or different techniques may be used to visualize the bone implant placement or the placement of the composition as is used to assess the repair progress of the bone defect. Furthermore, more than one technique may be used for each step. For example, PFCs are detected by $^{19}$F magnetic resonance imaging (MRI) at lower concentrations than PFCs are detected by X-ray fluoroscopy, thus MRI may be used for tracking of initial placement of PFC-containing implants. Follow-up visualization of the PFC-containing implant sites may be assessed by X-ray fluoroscopy without radiographic interference from any remaining PFC at the implant sites.

The temporary radiopaque agent used in the bone implant or the composition for implanting in a bone defect may be judiciously selected to provide increased radiopacity for one imaging technique over the other. Thus, the bone implants or compositions for implanting in a bone defect may be visualized by any imaging techniques during the bone graft placement to provide images of both the bone graft placement and an initial view of the non-healed site without radiographic interference by the radiopaque implant.

The radiopacity of the bone implants or compositions for implanting in a bone defect prepared may range from about the equivalent thickness of about 0.1 mm of aluminum to about 11 mm of aluminum, to about the equivalent thickness of about 0.3 mm of aluminum to about 8 mm of aluminum, to about the equivalent thickness of about 0.5 mm of aluminum to about 5 mm of aluminum, or to about the equivalent thickness of about 0.7 mm of aluminum to about 3 mm of aluminum.

Embodiments of the present invention may be used on any animal patient. Animals includes food production animals (e.g. cattle, pigs, lamb, fowl (chickens, turkeys, etc.), fish, and shellfish, companion animals (e.g. dogs, cats, and horses), working animals (e.g. dogs and horses), other animals (e.g. murid, an equid, a lagomorphs) and humans. Preferably, the animal is a human. The bone defects subject to the present invention may be located in an extremity, the pelvis, the spine, the posterolateral spine, the craniomaxillofacial region, the cranium or other skeletal defect in the animal.

In still other embodiments of the present invention, prior to the implantation step, the bone implant or the composition for implanting in a bone defect is produced by contacting the bone graft substitute with the temporary radiopaque agent. The bone implant or the composition for implanting in a bone defect may be produced immediately before it is implanted into the patient, or several hours, days, weeks, or years before it is implanted into a patient.

Another aspect of the invention is a method of preparing a bone implant containing a temporary radiopaque agent, comprising contacting a bone graft substitute with the temporary radiopaque agent, wherein the temporary radiopaque agent is in a form selected from the group consisting of a neat solution, an undiluted solution, an emulsion, a suspension, a slurry, and a gel, and wherein the bone graft substitute is radiolucent.

In some embodiments during the process to make the bone implant, the temporary radiopaque agent may be in the form of a suspension, a slurry, a gel, an emulsion, mixtures of temporary radiopaque agent(s) or the temporary radiopaque agent(s) with other bioactive substances. These forms may be generated in a carrier of water or aqueous solutions, non-water based media and combinations thereof. Suitable water or aqueous solutions include, but are not limited to, phosphate buffered saline, saline, and balanced salt solutions. Non-water based solvents, such as water miscible solvents including, but are not limited to, acetonitrile, dimethyl sulfoxide, ethanol, methanol, glycerol, isopropanol, tetrahydrofuran, acetone, and mixtures thereof. Other suitable carriers include diethyl ether, ethyl acetate, hexanes, and pentane, which may be mixed with the aqueous solutions and non-water based solvents. The carriers may be combined to create a mixture comprising between about 0.5% to about 95% by weight of the bone implant or the composition for implanting in a bone defect, between about 1% by weight to about 90% by weight of the bone implant or the composition for implanting in a bone defect, or about 10% by weight to about 85% by weight of the bone implant or the composition for implanting in a bone defect. Slurries, and similarly gels, may be generated in reverse phase polymer carriers, such as poloxamers. The amount of reverse phase polymer carriers used in the gels or slurries may comprise an amount between about 0.5% by weight to about 95% by weight of the bone implant or the composition for implanting in a bone defect, to about 1% by weight to about 90% by weight of the bone implant or the composition for implanting in a bone defect, or about 10% by weight to about 85% by weight of bone implant or the composition for implanting in a bone defect. Additional additives which may be used to generate slurries and gels include, but are not limited to, alginate, dextran, gelatin, lecithin, and hyaluronate. The amount of additional additives may comprise an amount of about 0.5% by weight to about 95% by weight of the bone implant or the composition for implanting in a bone defect, between about 1% by weight to about 90% by weight of the bone implant or the composition for implanting in a bone defect, or about 10% by weight to about 85% by weight of the bone implant or the composition for implanting in a bone defect.

Emulsions of the temporary radiopaque agent with other bioactive substances may be generated by homogenization of the temporary radiopaque agent, the bioactive substance and at least one emulsifying agent or surfactant. Suitable emulsifying agents and/or surfactants include, but are not limited to, alginate, carboxymethyl cellulose, phospholipids, poly(lactide-co-glycolide)s, polylactides, polycaprolactones, polyorthoesters, and lecithins. The amount of emulsifying agents or surfactants to generate emulsions may comprise an amount of about 0.1% by weight to about 99% by weight of the bone implant or the composition for implanting in a bone defect, to about 0.5% by weight to about 95% by weight of the bone implant or the composition for implanting in a bone defect, or about 1% by weight to about 90% by weight of the bone implant or the composition for implanting in a bone defect.

To aid in the dissipation of the temporary fluoroscopic dye under controlled release conditions, the dye may be suspended, slurried, dissolved, or emulsified in the presence of at least one biodegradable polymer. Volatile components may be removed such that the bone graft substitute doped with the temporary radiopaque agent will be fully or partially encapsulated by the temporary radiopaque agent and perhaps bioactive substances. In this manner, the dissipation of the temporary radiopaque agent from the bone implant or the composition for implanting in a bone defect following the implant placement may be tuned to a desired dissipation rate. It is well known in the art that the rate of biodegradation of a polymeric system can be controlled by modifying the chemical makeup of the polymeric system. For example, polymeric systems with shorter polymer chain lengths typically biodegrade faster than longer chain lengths. Similarly, more hydrophilic polymers typically biodegrade faster than more hydrophobic polymers. Therefore, the rate of biodegradation of the temporary radiopaque agent can be easily controlled to match the exact requirements for a given system.

In some embodiments during the manufacturing of the bone implant, the temporary radiopaque agent may be in a form selected from the group consisting of an emulsion, a suspension, a slurry and a gel. The bone graft substitute may be contacted with the temporary radiopaque agent for between about 30 seconds to about two hours. In some embodiments, a solution of the temporary radiopaque agent may be injected into and/or onto the bone graft substitute. In still other embodiments, the temporary radiopaque agent may be perfused through the bone graft substitute by exerting a vacuum upon the bone graft substitute. The vacuum pressure may be between about 0.1 mTorr and about 760 Torr and applied for between about 60 seconds and about 48 hours.

Some embodiments include freezing the bone implant or the composition for implanting in a bone defect at a temperature between about 0° C. and about −100° C. to form a frozen bone implant or the composition for implanting in a bone defect. The frozen bone implant or the frozen composition for implanting in a bone defect may be stored at a temperature between about 0° C. and about −100° C. until its use at which time the implant would be thawed. In some embodiments, the frozen bone implant or the frozen composition for implanting in a bone defect may be lyophilized to form a frozen lyophilizing bone implant or the frozen lyophilizing composition for implanting in a bone defect. Prior to implantation, the frozen lyophilizing bone implant or the frozen lyophilizing composition may be rehydrated with a rehydration solution. The rehydration solution may be an aqueous buffer, biocompatible water miscible solvents, and combinations thereof.

In still other embodiments, at least one surface of the bone graft substitute may be activated using a cold gas plasma treatment. The treatment may include direct surface functionalization of the bone graft substitute with the temporary radiopaque agent; an initial cold gas plasma treatment with a small organic molecule followed by a cold gas plasma treatment with the temporary radiopaque agent; or an initial cold gas plasma activation of a surface of the bone graft substitute by an initial cold gas plasma treatment with a small organic molecule to form a plasma treated bone graft substitute prior to contacting with the temporary radiopaque agent.

Another aspect of the invention is a composition comprising a radiolucent bone graft substitute and a temporary radiopaque agent, wherein the temporary radiopaque agent dissipates in less than about one month after it is implanted into a patient.

In embodiments, the radiopacity of the composition may be equivalent to the thickness of between about 0.1 to about 11 mm of aluminum, between about 0.3 to about 8 mm of aluminum, between about 0.5 to about 5 mm of aluminum, or between about 0.7 to about 3 mm of aluminum.

Following placement of the bone implant or the composition for implanting in a bone defect, the radiopaque agent dissipates to the radiopacity equivalent of between about 0.01 mm of aluminum to about 0.5 mm of aluminum within about one month of the placement of the bone graft substitute. In some embodiments, the temporarily radiopaque agent dissipates to less than the radiopacity equivalent of about 0.5 mm of aluminum, less than about 0.3 mm of aluminum, less than about 0.1 mm of aluminum, less than about 0.05 mm of aluminum, less than about 0.01 mm of aluminum.

EXAMPLES

Example 1

Preparation of a Bone Implant or the Composition for Implanting in a Bone Defect Containing a Temporary Radiopaque Agent(s)

Combining a bone graft substitute with temporary radiopaque agents may be accomplished by numerous routes. Any of the following methods may include other bioactive substances as desired.

Method 1

Place a bone graft substitute into an emulsion, suspension, slurry, or gel containing a temporary radiopaque agent or mixture of temporary radiopaque agents for between about 30 seconds to about two hours. Remove the coated or embedded bone graft substitute. This preparation of the implant material may be performed at some time prior to the surgical intervention or the steps may be performed immediately prior to implantation.

Method 2

Inject a neat solution of the temporary radiopaque agent or mixture of undiluted temporary radiopaque agents onto or into the bone graft substitute. This preparation of the implant material may be performed at some time prior to the surgical intervention or the steps may be performed immediately prior to implantation.

Method 3

Place the bone graft substitute in a temporary radiopaque agent(s) suspension, gel, slurry, or emulsion. The combination of bone graft substitute and temporary radiopaque agent(s) is frozen. The implant material would then be thawed prior to surgical implantation.

Method 4

Repeat Method 3 to prepare a frozen implant material. Lyophilize the frozen implant to increase the stability of the composition. The implant material would then be rehydrated prior to implantation. Suitable rehydration solutions include, but are not limited to, aqueous buffers and biocompatible water miscible solvents.

Method 5

Place the bone graft substitute in a temporary radiopaque agent(s) suspension, gel, slurry, or emulsion then the liquid carriers of the temporary radiopaque agent(s) are thoroughly perfused through the bone graft substitute by vacuum. The bone graft substitute coated or embedded implant may then be (a) stored for later use, (b) used immediately for surgical implantation, (c) frozen and later thawed for use, (d) frozen, lyophilized, stored, and rehydrated prior to use.

Method 6

Coat the bone graft substitute with the temporary radiopaque agent by a cold gas plasma treatment process. The cold gas plasma process may consist of direct surface functionalization of the bone graft substitute with the temporary radiopaque agent(s), activation of the surface of the bone graft substitute by cold gas initial plasma treatment with a small organic molecule followed by plasma treatment with the temporary radiopaque agent(s), activation of the surface of the bone graft substitute by initial cold gas plasma treatment with a small organic molecule followed by placement of the now plasma treated bone graft substitute into a neat solution, suspension, gel, slurry or emulsion of the temporary radiopaque agent(s), or other plasma treatment techniques known in the existing art. The plasma coated bone graft substitute may then be (a) stored for later use, (b) used immediately for surgical implantation, (c) frozen and later thawed for use, (d) frozen, lyophilized, stored, and rehydrated prior to use.

Example 2

Method of Use

The bone implant or the composition for implanting in a bone defect fabricated according to one of the methods of Example 1 is implanted into a bone void or defect. Following and during implantation, the position of the implant is visualized by medical imaging. For subsequent assessment of the bone healing or fusion, the surgical site is visualized by medical imaging following a suitable post-operative recovery period (typically about three months to about six months).

Example 3

Contrast Agents on Bone Grafts

Figure 1:
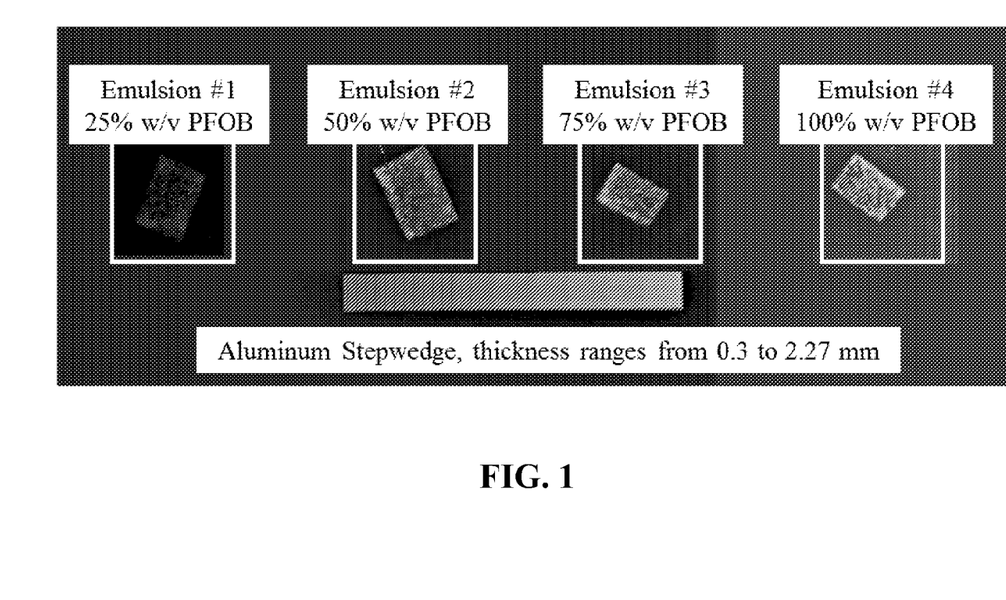
FIG. 1 illustrates the radiopacity of bone grafts hydrated in perfluorooctyl bromide containing emulsions.

Four emulsions were prepared by combining perfluorooctyl bromide (PFOB), lecithin, glycerol and water. The compositions of the different emulsions are listed in the Table 2. For each emulsion, the biphasic mixture of all components was vortexed (Maximix II Vortex Mixer) vigorously for several minutes. The resultant homogenous emulsion was then used to hydrate lyophilized, demineralized cancellous bone strips (OsteoSponge®, Bacterin International, Inc.). X-ray images of the hydrated bone grafts were acquired. The increased radiopacity for the grafts with increased PFOB content is illustrated in FIG. 1. The intravenous half-life of PFOB varied by dosage—in an intravascular model PFOB had a half-life of 9.4 hours for a 1.2 g/kg dose (*Anesth and Analg.* 2000, 91, 804-811). The radiopacity of the described implants is anticipated to dissipate within hours following implantation.

TABLE 2

| Component | Emulsion #1 | Emulsion #2 | Emulsion #3 | Emulsion #4 |
|---|---|---|---|---|
| | Approximate % w/v of the component | | | |
| PFOB | 25 | 50 | 75 | 100 |
| Lecithin | 4 | 4 | 9.1 | 9.1 |
| Glycerol | 2.21 | 2.21 | 1 | 1 |
| Water | 80 | 70 | 50 | 40 |

Example 4

Samples with and without Bioglass

Figure 2:
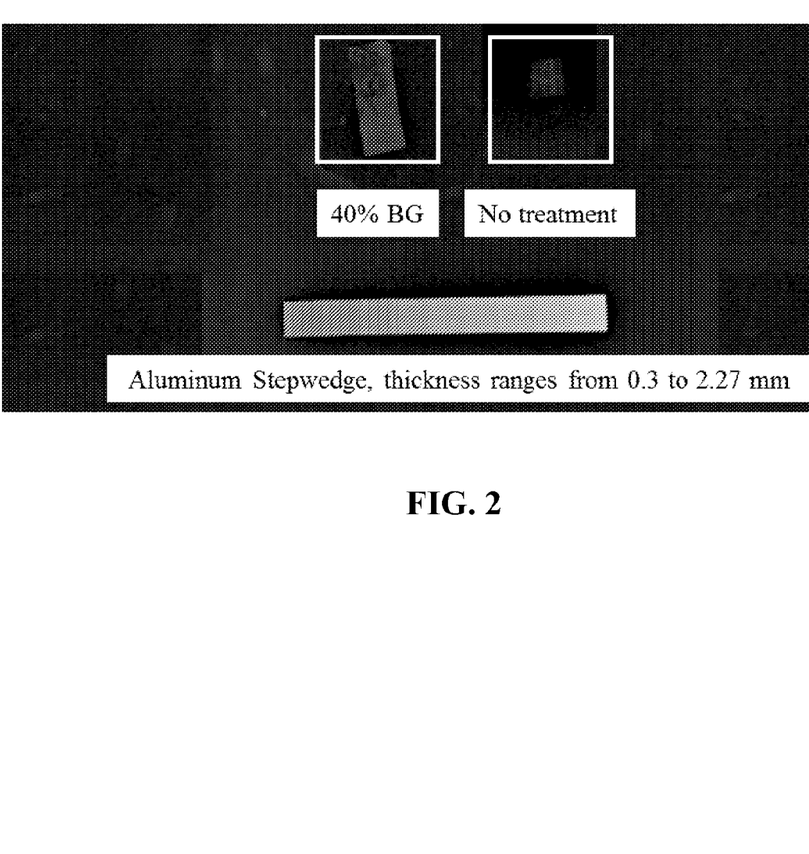
FIG. 2 illustrates the radiopacity of a bone graft hydrated with an aqueous suspension of bioglass and the radiopacity of an untreated demineralized, cancellous bone graft.

A lyophilized, demineralized cancellous bone strip (OsteoSponge®, Bacterin International, Inc.) was hydrated in a suspension of 40% w/v of 45S5 bioglass (BG) in water. A lyophilized, demineralized cancellous bone strip was untreated for comparison. X-ray images of the bone grafts were acquired side-by-side. The increased radioopacity for the graft with 40% BG is illustrated in FIG. 2.

The foregoing discussion of the disclosure has been presented for purposes of illustration and description. The foregoing is not intended to limit the disclosure to the form or forms disclosed herein. In the foregoing Description of the Embodiments for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

What is claimed is:

1. A composition of an implant comprising:
a radiolucent bone graft substitute comprising at least one of a collagen, a fibrin, a demineralized bone matrix, or combinations thereof; and
a temporary radiopaque agent that dissipates in less than about six months after the composition is implanted in a patient to less than 99% of an initial amount of the radiopaque agent in the composition, wherein the temporary radiopaque agent is in an emulsion, and wherein an emulsifying agent is selected from the group consisting of an alginate, a carboxymethyl cellulose, a phospholipid, a poly(lactide-co-glycolide), a polylactide, a polycaprolactone, a polyorthoester, a lecithin, and combinations thereof, and wherein an amount of the emulsifying agent is between about 0.5% by weight to about 95% by weight of the composition.

2. The composition of claim 1, wherein the radiolucent bone graft substitute is coated with the temporary radiopaque agent.

3. The composition of claim 1, where the temporary radiopaque agent dissipates over the course of minutes to months so that visualization of new bone formation is unobstructed by the temporary radiopaque agent.

4. The composition of claim 1, wherein the temporary radiopaque agent dissipates within about fourteen days.

5. The composition of claim 1, wherein the radiolucent bone graft substitute further comprises an additive selected from the group consisting of a biodegradable polymer and a biodegradable polymer mixture.

6. The composition of claim 1, wherein the radiolucent bone graft substitute is the collagen.

7. The composition of claim 1, wherein the radiolucent bone graft substitute is the fibrin.

8. The composition of claim 1, wherein the radiolucent bone graft substitute is the demineralized bone matrix.

9. The composition of claim 8, wherein the demineralized bone matrix is allogeneic.

10. The composition of claim 8, wherein the demineralized bone matrix is xenogeneic.

11. The composition of claim 8, wherein the demineralized bone matrix is at least partially demineralized with about 1% to about 90% of an original mineral content of the bone removed.

12. The composition of claim 8, wherein the demineralized bone matrix is in a form selected from the group consisting of a block, a cone, a strip, a cylinder, a wafer, a bone putty, a bone paste, shredded fibers, a plurality of ground particles and combinations thereof.

13. The composition of claim 8, wherein the demineralized bone matrix is ground into particles sized between about 0.2 mm and about 15 mm.

14. The composition of claim 1, wherein the temporary radiopaque agent is covalently bound to a carrier and/or additive.

15. The composition of claim 1, wherein the temporary radiopaque agent is ionically bound to a carrier and/or additive.

16. The composition of claim 1, wherein the temporary radiopaque agent comprises a material selected from the group consisting of iodine, gadolinium, barium, bismuth, perfluorocarbon, and combinations thereof.

17. The composition of claim 16, wherein the material is the perfluorocarbon and is selected from the group consisting of perfluorooctyl bromide, perfluorohexyl bromide, perfluorooctane, perfluoropentane, perfluorohexane, perfluorodecalin, perfluorotributylamine, perfluorotriisopropylamine, perfluoro-crown ethers salts thereof and combinations thereof.

18. The composition of claim 16, wherein the perfluorocarbon is a perfluoro-crown ether and contains at least one of 12-crown ether, 15-crown ether, or 18-crown ether.

19. The composition of claim 1, wherein the temporary radiopaque agent dissipates to a radiopacity of less than the equivalent of 0.1 mm of aluminum.

20. The composition of claim 1, wherein the composition further comprises a bioactive substance selected from the group consisting of antibiotics, anti-infective agents, hormones, growth factors, cells and combinations thereof.

21. The composition of claim 1, wherein the radiolucent bone graft substitute and the temporary radiopaque agent are frozen.

22. The composition of claim 1, wherein the radiolucent bone graft substitute and the temporary radiopaque agent are lyophilized.

23. The composition of claim 1, wherein the radiolucent bone graft substitute and the temporary radiopaque agent are rehydrated.

24. The composition of claim 1, wherein a radiopacity of the composition is equivalent to the thickness of between about 0.1 to about 11 mm of aluminum.

25. The composition of claim 1, wherein a radiopacity of the composition is equivalent to the thickness of between about 0.3 to about 8 mm of aluminum.

26. The composition of claim 1, wherein a radiopacity of the composition is equivalent to the thickness of between about 0.5 to about 5 mm of aluminum.

27. The composition of claim 1, wherein a radiopacity of the composition is equivalent to the thickness of between about 0.7 to about 3 mm of aluminum.

28. The composition of claim 1, wherein the temporary radiopaque agent is selected from the group consisting of a gadolinium, a bismuth, and combinations thereof.

29. The composition of claim 1, wherein the temporary radiopaque agent encapsulates the radiolucent bone graft substitute.

30. The composition of claim 1, wherein the temporary radiopaque agent is selected from the group consisting of a perfluorooctane, a perfluoropentane, a perfluorohexane, a perfluorodecalin, a perfluorotributylamine, a perfluorotriisopropylamine, a perfluoro-crown ethers salt thereof and combinations thereof.

31. The composition of claim 1, wherein a concentration of the temporary radiopaque agent is from about 50% to about 99% by weight of the composition.

32. The composition of claim 1, wherein the radiopaque agent dissipates to less than about 95% of an initial amount of the radiopaque agent in the composition.

33. The composition of claim 1, wherein the radiopaque agent dissipates to less than about 90% of an initial amount of the radiopaque agent in the composition.

34. The composition of claim 1, wherein the radiopaque agent dissipates to less than about 85% of an initial amount of the radiopaque agent in the composition.

35. The composition of claim 1, wherein the radiopaque agent dissipates to less than about 80% of an initial amount of the radiopaque agent in the composition.

36. The composition of claim 1, wherein the radiopaque agent dissipates to less than about 70% of an initial amount of the radiopaque agent in the composition.

37. The composition of claim 1, wherein the radiopaque agent dissipates to less than about 60% of an initial amount of the radiopaque agent in the composition.

38. The composition of claim 1, wherein the radiopaque agent dissipates to less than about 50% of an initial amount of the radiopaque agent in the composition.

39. The composition of claim 1, wherein the radiopaque agent dissipates to less than about 40% of an initial amount of the radiopaque agent in the composition.

40. The composition of claim 1, wherein the radiopaque agent dissipates to less than about 30% of an initial amount of the radiopaque agent in the composition.

41. The composition of claim 1, wherein the radiopaque agent dissipates to less than about 20% of an initial amount of the radiopaque agent in the composition.

42. The composition of claim 1, wherein the radiopaque agent dissipates to less than about 10% of an initial amount of the radiopaque agent in the composition.

43. The composition of claim 1, wherein an amount of the emulsifying agent is between about 1% by weight to about 90% by weight of the composition.

44. The composition of claim 5, wherein the biodegradable polymer or the biodegradable polymer mixture comprise an alginate, a hyaluronate, a polycaprolactone, a polyethylene glycol, a polyhydroxyalkanoate, a polyesteramide, a polylactide, a polyglycolide, a poly(lactide-co-glycolide), a polyorthoester, a polyoxazoline, a polyurethane, and combinations thereof.

45. The composition of claim 6, wherein the collagen is a scaffold.

46. The composition of claim 7, wherein the fibrin is a scaffold.

47. A composition of an implant comprising a radiolucent bone graft substitute comprising at least one of a collagen, a fibrin, a demineralized bone matrix, or combinations thereof and a temporary radiopaque agent, wherein the radiopaque agent is present in an emulsion in an amount ranging from about 50% to about 90% by weight of the composition, wherein the radiopaque agent dissipates to between about 10% and 99% of an initial amount of the composition in between 30 minutes and six months after the composition is implanted in a patient.

48. The composition of claim 47, wherein the radiopaque agent dissipates to between 20% and 90% of an initial amount of the composition.

49. The composition of claim 47, wherein the radiopaque agent dissipates to between 10% and 50% of an initial amount of the composition.

* * * * *